United States Patent
Chan

(10) Patent No.: US 8,932,648 B2
(45) Date of Patent: Jan. 13, 2015

(54) METHOD OF SELECTING PHOSPHATE BINDER AND ITS USES THEREOF

(75) Inventor: Keith Chan, Rockville, MD (US)

(73) Assignee: Globoasia, LLC, Rockville, MD (US)

( * ) Notice: Subject to any disclaimer, the term of this patent is extended or adjusted under 35 U.S.C. 154(b) by 1189 days.

(21) Appl. No.: 12/162,247

(22) PCT Filed: Jan. 26, 2007

(86) PCT No.: PCT/US2007/002158
§ 371 (c)(1),
(2), (4) Date: Jul. 25, 2008

(87) PCT Pub. No.: WO2007/089578
PCT Pub. Date: Aug. 9, 2007

(65) Prior Publication Data
US 2010/0136135 A1   Jun. 3, 2010

Related U.S. Application Data

(60) Provisional application No. 60/763,735, filed on Jan. 30, 2006.

(51) Int. Cl.
*A01N 59/16* (2006.01)
*A61K 33/24* (2006.01)
*C01B 25/00* (2006.01)
*C07D 407/00* (2006.01)
*C12Q 1/02* (2006.01)
*A01N 55/02* (2006.01)
*A61K 31/555* (2006.01)
*G01N 33/84* (2006.01)

(52) U.S. Cl.
CPC .......... *G01N 33/84* (2013.01); *G01N 2500/10* (2013.01); *G01N 2800/347* (2013.01)
USPC ........ 424/647; 423/323; 423/419.1; 549/418; 435/29; 514/184

(58) Field of Classification Search
CPC .............. G01N 33/84; G01N 2500/10; G01N 2800/347; A01N 59/16; A01N 55/02; A61K 33/24; A61K 31/555; C01B 25/00; C12Q 1/02
USPC ................ 424/647; 423/323, 419.1; 549/418; 435/29; 514/184
See application file for complete search history.

(56) References Cited

U.S. PATENT DOCUMENTS

| | | | |
|---|---|---|---|
| 4,970,079 A * | 11/1990 | Hem et al. ............... | 424/646 |
| 5,980,881 A * | 11/1999 | Mitsuka et al. ........... | 424/78.1 |
| 2006/0020026 A1 * | 1/2006 | Kwok et al. .............. | 514/502 |

OTHER PUBLICATIONS

Shah et al., (Biotechnol Prog. Jan.-Feb. 2006;22:186-198; ePub online Nov. 25, 2005).*
Glahn et al., (J Nutr Biochem. Feb. 11, 2000 (2):62-8).*
PCT International Search Report for GLOBOASIA, LLC, et al., International App'l No. PCT/US2006/002158, filed Jan. 26, 2007, Dated Sep. 25, 2007.
PCT Written Opinion of the International Searching Authority for GLOBOASIA, LLC, et al., International App'l No. PCT/US2006/002158, filed Jan. 26, 2007, Dated Sep. 25, 2007.
Shah et al., 2006, "Role of CaCo-2 Cell Monolayers in Prediction of Intestinal Drug Absorption", Biotechnology Progress, vol. 22(1):186-198.

* cited by examiner

*Primary Examiner* — Cherie M Stanfield
(74) *Attorney, Agent, or Firm* — Law Offices of Albert Wai-Kit Chan, PLLC

(57) ABSTRACT

A method of selecting or determining a candidate compound suitable for use as a phosphate binder is disclosed. The candidate compound includes ferric compounds, ferric compound complexes, and their derivatives, salts, analogs, and metabolites. The effectiveness of the candidate compound as a phosphate binder is evaluated by a method, comprising measuring and correlating reduction of phosphate concentration in solution and reduction of phosphate absorption in cells.

6 Claims, No Drawings

US 8,932,648 B2

METHOD OF SELECTING PHOSPHATE BINDER AND ITS USES THEREOF

This application is the National Stage of International Application NO. PCT/US2007/002158, filed Jan. 26, 2007, which claims benefit of U.S. Ser. No. 60/763,735, filed Jan. 30, 2006 the entire disclosure of which is incorporated by reference herein in its entirety.

Throughout this application, various references or publications are cited. Disclosures of these references or publications in their entireties are hereby incorporated by reference into this application in order to more fully describe the state of the art to which this invention pertains.

BACKGROUND OF THE INVENTION

Hyperphosphatemia is a serious and chronic medical condition in end-stage renal diseases. Although it is possible to increase the elimination of phosphate from the plasma in dialysis patient, this approach is severely limited by the fact that transfer of phosphate from the blood cells into plasma is the rate-limiting step (Pohlmeier and Vienken, Phosphate removal and hemodialysis conditions. Kidney Int. Suppl. 78:S190-194 (2001)). Therefore, a more promising route of treating phosphate overload is to decrease the absorption of phosphate. Phosphate is transported into the intestinal cells via a phosphate-sodium co-transporter, and transported across the basolateral membrane into the blood via a yet to be identified pathway (Murer et. al., Molecular aspects in the regulation of renal inorganic phosphate reabsorption: the type IIa sodium/inorganic phosphate co-transporter as the key player. Curr. Opin. Nephrol. Hypertens. 10:555-561 (2001)). The phosphate-sodium cotransporter is stimulated by 1,25-dihydroxycholecalciferol, an active metabolite of vitamin D, but the mechanism of this action is not entirely clear. Because phosphate is taken up by carrier-mediated pathways, the rate of absorption may not increase linearly with the concentration.

Presently, the therapy for managing phosphate absorption is through the use of precipitation agents such as aluminum, calcium (Malluche et. al., Hyperphosphatemia: pharmacologic intervention yesterday, today and tomorrow. Clin. Nephrol. 54:309-317 (2000)) and other heavy metal ions such as lanthanum, and a polymer-like materials such as sevelamer HCl, (a non-aluminum, non-calcium containing hydrogel or Renagel®) (Gallieni et. al., Sevelamer reduces calcium load and maintains a low calcium-phosphorus ion product in dialysis patients. J Nephrol. 14:176-183 (2001)). These agents have been shown to be beneficial but better agents are yet to be developed, because the available drugs are only partially effective.

SUMMARY OF THE INVENTION

A brief summary of the invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

This invention provides a method to determine whether a candidate compound is capable of binding phosphate, comprising the steps of measuring reduction of phosphate concentration in solution and reduction of phosphate absorption in cells. In one embodiment, the present invention provides a method of selecting a candidate compound capable of reducing phosphate absorption by 75%.

This invention also provides a dietary phosphate binder determined or identified according to the method described above.

This invention also provides a pharmaceutical composition comprising an effective amount of a compound determined to be a phosphate binder by the method described above and a pharmaceutically acceptable carrier.

This invention also provides a method for preventing, treating as stabilizing a subject who has phosphate imbalance, comprising administrating to said subject a compound determined to be a phosphate binder by the method described above.

DETAILED DESCRIPTION OF THE INVENTION

This invention provides a method of determining whether a candidate compound, such as a ferric compound, is capable of binding phosphate. Candidate compound includes, but is not limited to, PBF1681 (Panion and BF Biotech, Inc., Taiwan), and other ferric compounds, their salts, compounds, metabolites, or derivates. PBF1681, disclosed in U.S. Ser. No. 11/206,981, filed Aug. 18, 2005, and in WO 2004/07444, filed Feb. 18, 2004, is a dietary phosphate binder which has shown efficacy in treating hyperphosphatemia. U.S. Ser. No. 11/206,981 and WO 2004/07444 are hereby incorporated by reference in their entireties.

The method of determining whether a candidate compound is a potential dietary phosphate binder comprises: contacting the candidate compound with phosphate under conditions permitting binding of the candidate compound with phosphate; measuring reduction of phosphate concentration in the presence of the candidate compound in a variety of buffer or solution; contacting the candidate compound with Caco-2 cells in a phosphate solution; measuring reduction of phosphate absorption in the cell; and correlating reduction of phosphate concentration in solution with reduction of phosphate absorption in the Caco-2 cells, wherein direct correlation of phosphate reduction indicates that the candidate compound is a phosphate binder.

In general, ferric citrate is used as a standard for a phosphate binder in the above method. In one embodiment, the buffer or solution used in the above method is simulated gastrointestinal fluids. Preferably, measuring reduction of phosphate concentration in a variety of buffer or solution comprises determining Langmuir adsorption isotherm in said buffer or solution. Furthermore, measuring reduction of phosphate concentration or phosphate absorption may comprise equilibrium binding experiments or kinetic experiments.

Completing the above steps hag shown that ferric citrate and PBF1681 is a phosphate binder that was not previously known. An effective amount of a candidate compound identified by the above method (e.g. ferric citrate) in combination with a pharmaceutically acceptable carrier will comprise a pharmaceutical composition.

A "pharmaceutically acceptable carrier" means any of the standard pharmaceutical carriers. Examples of suitable carriers are well known in the art and may include, but are not limited to, any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules.

Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

This invention also provides a method for preventing, treating or stabilizing a subject (e.g. a mammal or a human) that have a phosphate imbalance, comprising administering to said subject a phosphate binder identified by the above method.

In general, one of ordinary skill in the art would be able to readily determine the dose and route of administering the phosphate binder identified by the method described herein. In one embodiment, the phosphate binder is ferric trimaltol, ferric bicarbonate, or ferric carbonate. Ferric trimaltol has been shown to be capable of correcting iron deficiency (Harvey et al., Ferric trimaltol corrects iron deficiency anaemia in patients intolerant of iron. Aliment. Pharmacol. Ther. 12:845-848 (1998)), whereas ferric carbonate and ferric bicarbonate can be used as arsenic or hydrogen sulfide removal media (U.S. Pat. Nos. 6,849,187; 5,948,269; 6,849,187; 5,948,269). However, these three ferric compounds have not been previously reported as phosphate binders.

This invention also provides use of a compound determined to be a phosphate binder by the method described herein in preparation of a medicament for treating a subject having phosphate imbalance. In one embodiment, the phosphate binder is ferric trimaltol, ferric bicarbonate, or ferric carbonate.

The invention being generally described, will be more readily understood by reference to the following examples which are included merely for purposes of illustration of certain aspects and embodiments of the present invention, and are not intended to limit the invention.

Example 1

Potential Ferric Compound Suitable as Dietary Phosphate Binder

Ideally, a ferric compound, salt or complex suitable for use as a dietary phosphate binder should have the following properties:

A. Ability to control hyperphosphatemia by binding dietary phosphate via the mechanism of reducing dietary phosphate absorption.

B. Ability to correct metabolic acidosis in renal failure.

C. Appropriate dissolution profile and availability of ferric ion to bind to dietary phosphate in the GI tract but with minimal systemic absorption of ferric either as ionic form or as salt form into the body.

D. The cationic form of the ferric compounds, salts or complex should be non-toxic to patient with chronic kidney disease and should not lead to concentration so high that cause side effect (Note: the estimated effective dose of PBF1681 (Panion and BF Biotech, Inc., Taiwan) is in the range of around 3-6 gm per day, which is equivalent to 116-174 mg of available ferric ion to bind with dietary phosphate).

E. Since relatively high oral dose (equivalent to 116-174 mg of Ferric ion) is required to bind to the dietary phosphate, the GI irritation potential for the ferric compound and salt would be another criterion to be considered.

The criteria for selecting candidate compounds which have potential as a dietary phosphate binder is provided below. Method of evaluating candidate ferric compounds, and their salts, derivatives, analogs, metabolites, to determine their effectiveness as a dietary phosphate binder is provided in Example 2.

Criteria for Selecting Phosphate Binders

1. The anion groups of the potential compounds should be non-toxic to patients with chronic kidney disease and should not lead to concentration so high that cause side effects. Anion groups such as ammonium, nitrate, sulfate, and etc should be avoided.

2. Appropriate solubility of potential ferric compounds in the GI tract condition. Compound should be with appropriate solubility to release ferric ion. Anion groups such as fatty acids with low solubility should be avoided.

3. Appropriate equivalence of ferric ion per gram of compound. The potential ferric compound should contain enough ferric ions to effectively bind with dietary phosphate. For example, PBF1681 contains 114 mg of ferric ion per capsule (500 mg). Compounds with ferric content less than 57 mg are excluded.

4. Metabolic acidosis is also a common problem in chronic kidney disease patients. Normal body pH range is between 6.0-7.5. The pKa of the anion group should be within the range. Acetic anion groups should be avoided.

The ferric compounds which satisfy the above criteria are: ferric trimaltol, ferric citrate, ferric bicarbonate, and ferric carbonate. The ferric content in the ferric trimaltol is the lowest among the four (65 mg Fe3±/500 mg compound). For ferric carbonate, the pKa of the carbonate group is beyond the normal body pH range (pKa=10.3). Ferric citrate and ferric bicarbonate are the ideal compounds with high ferric content and may ameliorate the acidosis problem in chronic kidney disease patients. See Table 2 below for a list of ferric compounds as potential phosphate binder, and a list of excluded compounds. Other compounds suitable for use as a dietary phosphate binder can be readily selected or determined by a person of ordinary skill in the art following the teaching of this invention. The potential of ferric compounds as dietary phosphate can be evaluated following the procedures described in Example 2.

Other ferric complex compounds suitable for use as a dietary phosphate binder can be readily selected or determined by a person of ordinary skill in the art following the teaching of this invention. An example of a suitable ferric complex compound is Iron Dextran which has been used for treating anemia. More recently, Ferrlecit® (sodium ferric gluconate complex in sucrose injection) was approved for the treatment of iron deficiency anemia. Of course, both Iron Dextran and sodium ferric gluconate complex are used to treat systemic disease and are not used as oral dietary phosphate binder. However, the potential of ferric complex compounds as dietary phosphate can be evaluated following the procedures described in Example 2.

TABLE 2

Ferric Compound List (excluding ammonium, nitrate, sulfate, and etc are excluded.)

| Compound | Molecular Formula | MW | $Fe^{3+}$ content per 500 mg compound | pKa of anionic group | Note & Consideration |
|---|---|---|---|---|---|
| Potential ferric compounds as phosphate binders after selection | | | | | |
| ferric trimaltol | Fe(C6H5O3)3 | 431 | 65 | Not found | Low $Fe^{3+}$ content |
| ferric citrate | FeC6H4O7 | 245 | 114 | pKa = 6.4 | |

TABLE 2-continued

Ferric Compound List (excluding ammonium, nitrate, sulfate, and etc are excluded.)

| Compound | Molecular Formula | MW | $Fe^{3+}$ content per 500 mg compound | pKa of anionic group | Note & Consideration |
|---|---|---|---|---|---|
| *ferric bicarbonate | Fe(CHO3)3 | 239 | 117 | pKa = 6.3 | |
| *ferric carbonate | Fe2(CO3)3 | 292 | 191 | pKa = 10.3 | pKa > 7.5 (normal body pH range) |
| Ferric compounds that are excluded | | | | | |
| *ferric oleate | Fe(C18H33O2)3 | 899 | 31 | Not found | $Fe^{3+}$ < ½ PBF1681 |
| ferric gluconate | Fe(C6H11O7)3 | 641 | 44 | pKa = 12.64 | $Fe^{3+}$ < ½ PBF1681 |
| *ferric histidinate | Fe(C6H8N3O2)3 | 518 | 54 | pKa = 1.8 | $Fe^{3+}$ < ½ PBF1681 |
| ferric octoate | Fe(C8H15O2)3 | 485 | 58 | Not found | $Fe^{3+}$ < ½ PBF1681 |
| *ferric aspartate | Fe(C4H6NO4)3 | 452 | 62 | pKa = 1.99 | May deteriorate acidosis (pKa < 6) |
| *ferric picolinate | Fe(C6H4NO2)3 | 422 | 66 | pKa = 3.98 | May deteriorate acidosis (pKa < 6) |
| ferric acetylacetonate | Fe(C5H8O2)3 | 356 | 78 | Not found | Toxic |
| ferric choline citrate | FeC11H24NO8+ | 354 | 79 | Not found | Fatty acid with solubility concerns |
| ferric EDTA | FeC10H13N2O8 | 345 | 81 | Not found | Safty concerns if consuming in large dose |
| ferric HEDTA | FeC10H15N2O7 | 331 | 85 | Not found | Safty concerns if consuming in large dose |
| *ferric triglycinate | Fe(C2H4NO2)3 | 278 | 100 | pKa = 2.35 | May deteriorate acidosis (pKa < 6) |
| *ferric malate | Fe2(C4H4O5)3 | 508 | 110 | pKa = 3.4 | May deteriorate acidosis (pKa < 6) |
| ferric acetate | Fe(C2H3O2)3 | 233 | 120 | pKa = 4.8 | May deteriorate acidosis (pKa < 6) |
| ferric ascorbate | FeC6H7O6+2 | 230 | 121 | pKa = 4.04 | May deteriorate acidosis (pKa < 6) |
| *ferric fumarate | Fe2(C4H2O4)3 | 448 | 125 | pKa = 3.02 | May deteriorate acidosis (pKa < 6) |
| ferric oxalate | Fe2(C2O4)3 | 393 | 142 | pKa = 1.25 | Toxic |
| ferric formate | Fe(CHO2)3 | 190 | 147 | pKa = 3.75 | May deteriorate acidosis (pKa < 6) |
| *ferric tartrate | Fe(C4H5O6)3 | 503 | 56 | pKa1 = 2.98 | May deteriorate acidosis (pKa < 6) |
| | Fe2(C4H4O6)3 | 556 | 100 | pKa2 = 4.34 | May deteriorate acidosis (pKa < 6) |
| *ferric succinate | Fe(C4H5O4)3 | 407 | 69 | pKa1 = 4.21 | May deteriorate acidosis (pKa < 6) |
| | Fe2(C4H4O4)3 | 460 | 122 | pKa2 = 5.64 | May deteriorate acidosis (pKa < 6) |

Example 2

System for Evaluating Absorption of Phosphates In Vitro

Hyperphosphatemia has been shown to be associated with increased risk of mortality in hemodialysis patients and increased cardiovascular risk. The normalization of phosphate level in the plasma is very important for managing patients suffering from severe renal disease. Because absorption of phosphate from the food exceeds the elimination through a hemodialysis treatment, a chronic phosphate overload exists for the majority of hemodialysis patients.

A methodology for determining how the absorption of phosphate can be reduced by decreasing the amount of phosphate available for absorption (and/or amount of phosphate absorption), comprises the following phases:

Phase I. Establish an in vitro method to measure phosphate concentration in solution in the presence of various candidate compounds and to determine how amounts of phosphate in solution may be reduced in the presence of the candidate compounds.

Phase I Further Comprises:

1. Determining how method(s) reported in the literature measure unbound inorganic phosphate (free and potentially absorbable), for example, using a kit from Sigma, can be adapted for determination of free and unbound inorganic phosphates. Determining if method utilized in measuring phosphate in vivo can be indirectly transferred to estimating phosphate concentration from colloidal solution (or suspension) and polymer solution (suspension). Determining the effects of pH and buffers (e.g., simulated gastric fluid) on the measurement of phosphate. Establishing a method such that the linear response range will be from 10-0.1 mM. Normally, the plasma phosphate concentration in human is 1 mM, and patients with severe renal diseases may have level triple the normal phosphate concentration. Because of the need to separate soluble phosphate from colloidal particles and polymers, equilibrium dialysis will be employed. Therefore, the concentration of phosphate measured will be equilibrium concentrations. This method of measuring concentration will be verified with high speed (100,000×g) centrifuge whenever possible.

2. Characterizing the potentials of candidate compounds in reducing phosphate concentrations in vitro. Determining the Langmuir adsorption isotherm for each tested compound in several buffers. Salts, calcium citrate and magnesium chloride will be used; two polymers, sevelamer and a positively charged polymer hydrogel; two colloidal solutions, aluminum oxide and lanthanum oxide; and three negative control, sodium chloride, a negatively charged hydrogel, and a negatively charged colloidal solution.

Phase II. Evaluate the potentials of various candidate compounds/agents in reducing the concentration of phosphate in a variety of buffer and simulated gastrointestinal fluids.

Phase II Further Comprises:

1. Measuring and ranking the potentials of candidate compounds/agents in reducing phosphate concentrations against the standard substrates used in phase I.

2. Evaluating the effectiveness of the method established in Phase I in selecting compounds with potential to decrease soluble phosphate in a solution.

Phase III. Determine and verify potential of model substrates in reducing the absorption of phosphates in the Caco-2 model.

Phase III Further Comprises:

1. Correlating the amount of phosphate in solution with amount of phosphate absorbed in the Caco-2 model in the absence or presence of selected candidate compounds with distinctive ability to change the phosphate concentration in a solution. Only pH values and conditions shown to be effective in reducing phosphate concentration will be use in this aim to reduce the number of studies necessary.

2. Determining which mode of decreasing phosphate concentrations will translate better into decreasing phosphate absorption in the Caco-2 model. Theoretically, those compounds that produced the most precipitation are expected to cause the largest decrease in phosphate absorption. However, this may be confounded by factors such as equilibrium constants. If phosphate could be adsorbed and deadsorbed rapidly by a compound, that compound may be effective in reducing phosphate concentration in an equilibrium system, but may not be the best in a dynamic system such as Caco-2, where concentration of phosphate will change with time.

Example 3

In Vitro Equilibrium Binding and Kinetic Studies

Determine the Common Phosphate Content in the Diet of a Population

For example, the phosphate content in a Normal American Diet is determined (from literature). This information will be used as the amounts of phosphate expected in the normal diet intake of a given population from each meal. Various amounts, such as 1×, 2×, 4×, etc., will be used in the in vitro equilibrium and kinetic studies. Various binding agents will then be tested for its equilibrium binding and kinetics to phosphate. Assuming that the phosphate will either bind to the binding agents as precipitate or entrapped into the polymer type of binding agents, one can measure either the disappearing of phosphate or binding agents before or after physical removal of precipitates or complex. Analytical method to determine phosphate or binding agents will be considered and priority will be give to measuring phosphate first.

Media Used in These Studies

The following media may be considered in the studies (provided in increasing complicity): water, simulated gastric fluid with and without enzyme, simulated intestinal fluid with and without enzyme, and the possibility of adding bile and fatty acids. Note: SGF and SIF may already contain phosphate. Additional phosphate from diet will be added to the media.

In Vitro Equilibrium Binding Experiments

This experiment will be conducted under conditions of constant time and varying concentrations of binding agents. The volume of the test medium should be constant at 250 ml. All experiments should be carried out at 37 degree C.

In Vitro Kinetic Experiments

This experiment will be conducted under constant concentration of binding agents with varying times of observation. At least three constant concentrations of binding agents should be used.

Feasibility and Establishment of the Testing System

The feasibility of equilibrium binding and kinetic experiments will be evaluated and validated using standard binding agents such as salts of aluminum, calcium, lanthanum, and polymer-like materials such as Sevelamer HCl. After the model is established, various binding agents may be tested in the system.

Protocol for Testing Various Binding Agents

Once the test system has been established, a standard protocol will be established in evaluating various binding agents for their capacity and kinetics in binding phosphate in vitro. At this stage, Ca citrate and Sevelamer may be used as positive controls.

Data Treatment and Analysis

Monomolecular adsorption of adsorbate (phosphate) molecules from solution, at constant temperature, on to an adsorbent (binding agent) can be described by Langmuir-type equation, as follows:

$$X/m = (k1\ k2\ Ceq)/(1 + k1\ Ceq)$$

$$\text{Or } Ceq/(x/m) = [1/(k1\ k2)] + [Ceq/k2], \text{ where}$$

Ceq=concentration of the adsorbate (phosphate) remaining in the solution at equilibrium;
x=the amount of adsorbate bound to the adsorbent (binding agent); and
m=the amount of adosrbent used.

The constant, k1, is defined as the adsorption coefficient or affinity constant and is related to the magnitude of the forces involved in the binding process.

The Langmuir-capacity constant, k2, indicates the apparent maximum amount of adsorbate that can be adsorbed per unit weight of adsorbent. The k1 and k2 constants can be obtained by plotting Ceq/(x/m) versus Ceq Data and Parameters to be Reported Six observations with mean±SD for the following parameters should be obtained and reported for both the test and reference products:

Percent binding of adsorbate at each concentration;
Micromoles (or amounts) of adsorbate bound at each concentration;
Affinity constant k1 and capacity constant k2;
Coefficient of determination, r2, when linear regression is used to determine k1 and k2.

What is claimed is:

1. A method to determine whether a candidate compound is capable of binding phosphate, comprising steps of:
   a) contacting the candidate compound with phosphate under conditions permitting binding of the candidate compound with phosphate;
   b) measuring reduction of phosphate concentration in the presence of the candidate compound in a variety of buffer or solution;
   c) contacting the candidate compound with Caco-2 cells in a phosphate solution;
   d) measuring reduction of phosphate absorption in the cells in the presence and absence of the candidate compound; and
   e) correlating reduction of phosphate concentration in solution with reduction of phosphate absorption in the Caco-2 cells, wherein a candidate compound that reduces both the phosphate concentration in solution and phosphate absorption in the Caco-2 cells is a phosphate binder.

2. The method of claim 1, wherein the buffer or solution is simulated gastrointestinal fluids.

3. The method of claim 1, wherein ferric citrate is used as a standard for a phosphate binder.

4. The method of claim 2, wherein ferric citrate is used as a standard for a phosphate binder.

5. The method of claim 1, wherein measuring reduction of phosphate concentration in a variety of buffer or solution comprises determining Langmuir adsorption isotherm in said buffer or solution.

6. The method of claim 1, wherein measuring reduction of phosphate concentration or phosphate absorption comprises equilibrium binding experiments or kinetic experiments.

* * * * *